US012343220B2

(12) United States Patent
Reid et al.

(10) Patent No.: US 12,343,220 B2
(45) Date of Patent: Jul. 1, 2025

(54) PROTECTIVE DEVICE FOR USE IN SURGERY APPLICATIONS

(71) Applicant: Relmat Pty Ltd, Sandringham (AU)

(72) Inventors: Luke Bartholomew Reid, Dolphin Heads (AU); Talei Virginia Reid, Dolphin Heads (AU)

(73) Assignee: Relmat Pty Ltd, Sandringham (AU)

( * ) Notice: Subject to any disclaimer, the term of this patent is extended or adjusted under 35 U.S.C. 154(b) by 243 days.

(21) Appl. No.: 17/913,248

(22) PCT Filed: Mar. 30, 2021

(86) PCT No.: PCT/AU2021/050280
§ 371 (c)(1),
(2) Date: Sep. 21, 2022

(87) PCT Pub. No.: WO2021/203160
PCT Pub. Date: Oct. 14, 2021

(65) Prior Publication Data
US 2023/0109813 A1    Apr. 13, 2023

(30) Foreign Application Priority Data

Apr. 6, 2020 (AU) ............................... 2020901079

(51) Int. Cl.
*A61B 90/40* (2016.01)
*A61B 46/20* (2016.01)

(52) U.S. Cl.
CPC .............. *A61B 90/40* (2016.02); *A61B 46/20* (2016.02)

(58) Field of Classification Search
CPC ......... A61B 90/40; A61B 46/20; A61B 46/30; A61B 46/40; A61B 2046/201;
(Continued)

(56) References Cited

U.S. PATENT DOCUMENTS 2,652,830 A * 9/1953 Koza ................... A62B 18/025
128/205.25
4,098,271 A * 7/1978 Maddock ................ A62B 9/00
128/205.13
(Continued)

FOREIGN PATENT DOCUMENTS

CN    106420065 A    2/2017
CN    108310577 A    7/2018
(Continued)

OTHER PUBLICATIONS

International Search Report and Written Opinion for Application No. PCT/AU2021/050280 dated Jul. 1, 2021 (23 pages).

(Continued)

*Primary Examiner* — Camtu T Nguyen
(74) *Attorney, Agent, or Firm* — Michael Best & Friedrich LLP

(57) ABSTRACT

Disclosed is a protective device comprising a seal portion adapted to be fitted over an orifice of patient, the seal portion having a perimeter adapted to be substantially sealed onto the patient. The protective device has one or more flexible sleeves which provides a substantially air-tight surround defining a passage in communication with said orifice. The or each flexible sleeve, at an end thereof which is distal from said seal portion, has an opening adapted to accept entry of a surgical instrument or scope into said passage. There is sealing member provided at said opening which is adapted to provide a seal around said surgical instrument or scope so that, in use, said surgical instrument or scope and said sealing member provide an airtight seal to substantially prevent leakage of particles from the passage.

11 Claims, 10 Drawing Sheets

(58) Field of Classification Search
CPC .............. A61B 2046/205; A61B 46/27; A61B 2046/234; A61B 2046/236
See application file for complete search history.

(56) References Cited

U.S. PATENT DOCUMENTS

| | | | |
|---|---|---|---|
| 4,998,538 A | 3/1991 | Charowsky et al. | |
| 5,299,582 A | 4/1994 | Potts | |
| 5,433,221 A | 7/1995 | Adair | |
| 5,676,133 A | 10/1997 | Hickle et al. | |
| 5,832,925 A * | 11/1998 | Rothrum | A61B 90/40 128/853 |
| 5,848,992 A | 12/1998 | Hart et al. | |
| 6,206,003 B1 * | 3/2001 | Burch | A61M 16/06 128/207.12 |
| 6,340,024 B1 * | 1/2002 | Brookman | A62B 17/04 128/201.15 |
| 7,316,233 B2 * | 1/2008 | Auerbach | A61B 46/27 128/853 |
| 8,365,734 B1 | 2/2013 | Lehman | |
| 2009/0126741 A1 | 5/2009 | Voic | |
| 2011/0290257 A1 | 12/2011 | Hillis et al. | |
| 2012/0330111 A1 | 12/2012 | Borody | |
| 2017/0071629 A1 | 3/2017 | Patel et al. | |

FOREIGN PATENT DOCUMENTS

| | | | |
|---|---|---|---|
| CN | 208611543 U | 3/2019 | |
| CN | 111329611 A | 6/2020 | |
| EP | 2532300 A2 | 12/2012 | |
| JP | 2019055291 A | 4/2019 | |
| WO | WO 2008/120108 A1 * | 10/2008 | ............. A61B 19/08 |

OTHER PUBLICATIONS

European Patent Office Extended European Search Report for Application No. 21785158.3, corresponding to International Application No. PCT/AU2021050280, dated Aug. 25, 2023 (27 pages).
International Preliminary Report on Patentability for Application No. PCT/AU2021050280 dated May 23, 2022 (4 pages).
Canadian Patent Office Action for Application No. 3171995 dated Oct. 10, 2024 (5 pages).

* cited by examiner

PROTECTIVE DEVICE FOR USE IN SURGERY APPLICATIONS

FIELD OF THE INVENTION

The present application relates to a protective device for use in surgical applications, and more specifically, although not exclusively, a protective device that provides substantial protection against the dissemination of particles from a patient during surgical or clinical applications.

BACKGROUND

Emerging research has found that viral particles present in the nose can be aerosolised, which greatly increases the viral load, thereby increasing potential for the spread and intensity of the virus. This is particularly problematic when the viral particles are a highly contagious, high morbidity virus (such as SARS-CoV-2, the coronavirus causing COVID-19) that sheds from the nose and mouth.

Ear, nose and throat (ENT) clinicians and surgeons, as well as clinicians and surgeons in gastroenterology applications and dentistry applications, for example, are uniquely susceptible to the COVID-19 virus but also any other virus that may be present in any opening or cavity around the face of a patient. Many of the most common clinical and surgical environments and methodologies used today that require investigation near a nose, mouth or inside a throat, including for example touching inside the nose, spraying inside the nose (e.g. an anaesthetising spray), cutting the nasal lining in surgical procedures, or using a scope that goes down a patient's throat in clinical and/or surgical applications, are exposed to a risk associated with an aerosolization of a virus present in the nose, mouth and/or throat of the patient.

Current solutions in the emerging ENT and anaesthetic literature include adopting Ebola protocols, e.g. getting gear on and off, processes for double glove and gown, face mask removal etc., increasing the use of personal protective equipment (PPE—e.g. drapes, powered air-purifying respirators, and eye wear), or using the "Kaiteki" position of a patient to administer to the nose and reduce aerosolization. All these solutions provide protective gear onto the surgical/clinical/healthcare staff and some current developing protocols are also extremely PPE heavy wherein, for example, additional drapes, masks, gloves are used. Some positive pressure rooms may also be used wherein surgeons may wear scuba gear to protect themselves from a virus carried by the patient during surgery and reduce the viral load.

However, the theatre and clinical/surgical environment including all instruments located within a three-metre radius of the patient need to be cleaned.

An improvement is needed.

SUMMARY

In a first aspect of the disclosure, there is provided a protective device comprising:
- a seal portion adapted to be fitted over an orifice of the patient, the seal portion having a perimeter adapted to be substantially sealed onto the patient;
- one or more flexible sleeve which provides a substantially air-tight surround defining a passage in communication with said orifice, the passage providing access to said orifice
- the or each flexible sleeve, at an end thereof which is distal from said seal portion, having an opening adapted to accept entry of a surgical instrument or scope into said passage;
- there being a sealing member provided at said opening which is adapted to provide a seal around said surgical instrument or scope so that, in use, said surgical instrument or scope and said sealing member substantially prevent leakage of particles from the passage.

In some embodiments, the seal portion comprises or is connected to one or more instrument ports, allowing access via said any one of said one or more instrument ports to said orifice, and the passage defined by the flexible sleeve is in communication with at least one of the one or more instrument ports.

At least one of the one or more flexible sleeves can be provided over a single one of the one or more instrument port. Additionally or alternatively, at least one of the one or more flexible sleeves can be provided over two or more instrument ports. Additionally or alternatively, two or more flexible sleeves can be provided over one of the one or more instrument port. In one embodiment, the protective device is adapted to prevent leakage of aerosolized discharges from the patient's orifice outside of a space enclosed by said protective device.

The respective flexible sleeve may be elongated.

In one embodiment, the perimeter of the seal portion is sealed onto the patient by way of any one or more of the following means: suction, negative pressure, static force, moisture, an adhesive material, a gel.

The seal portion may be adapted to be fitted over the patient's nose, mouth, or both.

In one embodiment, the seal portion includes an aperture adapted for allowing air inflow or delivery of air into the seal portion from an air delivery device. Alternatively, or simultaneously, the seal portion may include an aperture or vent adapted for insertion of, or connection with, a suction device to remove air or particles from inside the seal portion. Said aperture may be provided within a spout or a nozzle. In some embodiments, the seal portion, instrument port, and the flexible sleeve are of an integral or unitary construction.

The seal portion, at a part which is adapted to cover over the patient's orifice, can be made of a transparent material.

In some embodiments, the protective device can comprise a skirt adapted to be attached to the patient at a location which is outside the perimeter of the seal portion.

The sealing member may be retained within the opening of the passage, or coupled to the opening. The sealing member may be retained within the openings by being retained within an insert which is in turn retained within the opening. The retaining of the insert or the sealing member in the opening, or the retaining of the sealing member within the insert, maybe effected by means of adhesive, bonding, retention flanges, or by interlocking arrangements, etc.

The protective device in accordance with embodiments of the present disclosure seeks to provide safe and preferably re-sealable access to a patient's orifices, such as the nose, mouth and throat. The aim is to reduce the risk for the aerosolization and spread of viral pathogens from the patient towards the healthcare providers (e.g. surgeons, anaesthetics, theatre staff, healthcare staff, dentists, and clinicians), while facilitating access for the healthcare provider to perform the procedure. The protective device in accordance with embodiments of the present disclosure provides a barrier protection, or facilitates the establishing of barrier protection, between a patient and healthcare professionals during clinical examination, surgical procedures or any other healthcare related activity.

BRIEF DESCRIPTION OF THE DRAWINGS

Notwithstanding any other forms which may fall within the scope of the disclosure as set forth in the Summary, specific embodiments will now be described, by way of example only, with reference to the accompanying drawings in which.

DETAILED DESCRIPTION

Figure 1:
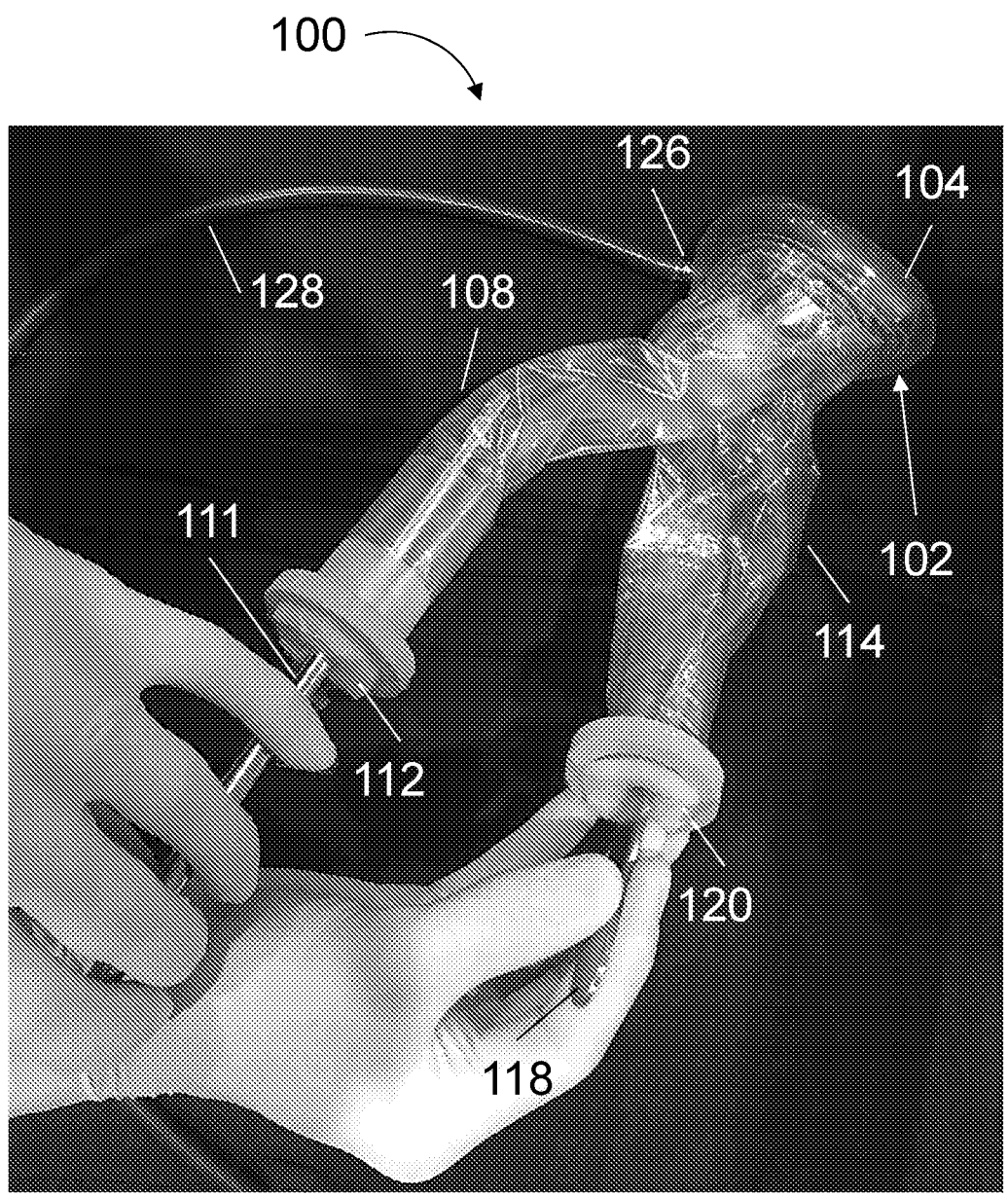
FIG. 1 is a perspective view of a protective device for use in healthcare applications, in accordance with an embodiment.

Embodiments of the present disclosure provide a protective device, which is adapted for use in healthcare applications, such as surgical or clinical procedures and would facilitate a safe environment in which to conduct essential surgery and clinical examination, which are of importance to protect the health and safety of health workers. This is of particularly pertinent during any disease outbreak.

In the FIGS., the same reference numerals will be used to identify the same parts. Combinations of different features may be included in different embodiments, and the same parts may have variations depending on embodiments.

With reference to FIGS. 1 to 5, there is illustrated an embodiment of the protective device 100 for use during surgical procedures (e.g. ENT surgery), clinical procedures, or examination. The protective device 100 comprises a seal portion 102 adapted to be fitted over an orifice of a patient (not shown). The seal portion 102 includes a cover which is preferably see through and which is adapted to be located over the patient's orifice. The seal portion 102 further includes a perimeter portion 104 (best seen in FIGS. 1, 2, and 3) which in use is adapted to come into contact with the patient and to be substantially sealed onto the patient. The seal portion 102 comprises an instrument port 106 that is arranged to allow access to said orifice of the patient. For example, the instrument port 106 comprises an opening 107 (see FIG. 3) through which a surgical instrument or scope can be inserted towards said orifice of the patient.

The terms "surgical instrument or scope" will be understood to encompass any instrument that may be used for and during surgical or clinical applications. It may for example include, but is not limited to, a scalpel or other mechanical cutter, a retractor, graspers, clamps, as well as a scope equipped with a CCD camera and/or emitting light or a fibre optic camera on a flexible tube.

Figure 6:
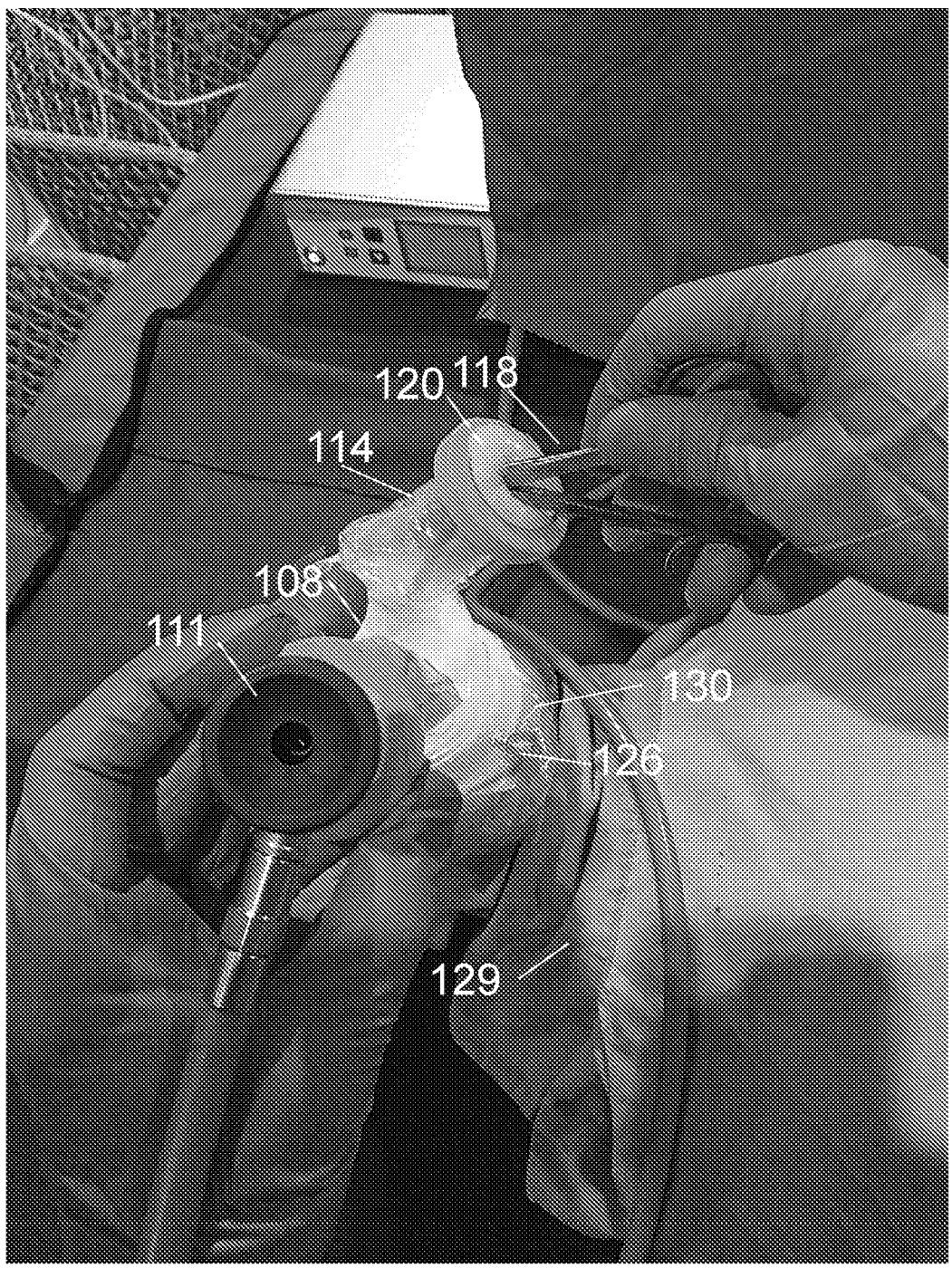
FIG. 6 is a perspective view of a protective device having two flexible sleeves, where one sleeve has inserted there in a surgical tool and the other has inserted therein a surgical scope.

As can be seen from FIG. 1, the instrument port 106 (best seen in FIG. 3) is attached to a flexible sleeve 108 which provides a substantially air-tight surround for, thus defining, a passage toward said orifice of the patient. The flexible sleeve 108, at an end thereof which is distal from the seal portion 102, include an opening. The opening is provided to accept entry of a surgical instrument or scope 111 into the passage, and toward the orifice of the patient. A sealing arrangement 112 is provided at this opening. For instance, FIG. 6 depicts an embodiment with two flexible sleeves 108, 114, respectively having inserted therein a surgical tool 118 and a scope 111. The sealing arrangement 112 is adapted to provide a seal around the surgical instrument 111, 118 (which maybe a tool or a scope depending on the application) so that, in use, the surgical instrument 111 and the sealing arrangement 112 provide an airtight seal to substantially prevent the leakage of particles from the passage.

In the embodiment illustrated in FIGS. 1 to 5, the instrument port 106 is further coupled with another flexible sleeve 114, which also provides a substantially air-tight surround for a passage to the orifice of the patient. The other flexible sleeve 114 also has an opening at an end that is distal from the seal portion 102, to accept entry of a surgical instrument 118 (or scope depending on the application) into the passage. A sealing member 120 is provided at the opening, the sealing member 120 being adapted to substantially close the entry to the passage, while providing a seal around the surgical instrument 118. In use, the surgical instrument 118 and said sealing member 120 provide an airtight seal to substantially prevent leakage of particles from the passage. In some embodiments, this is achieved by fitting distal instrument ports to the free ends (i.e., the ends distal from the seal portion 102) of the flexible sleeves 108, 114, to provide the access to the surgical tools whilst minimising leakage from inside the sleeves 108, 114.

Figure 4:
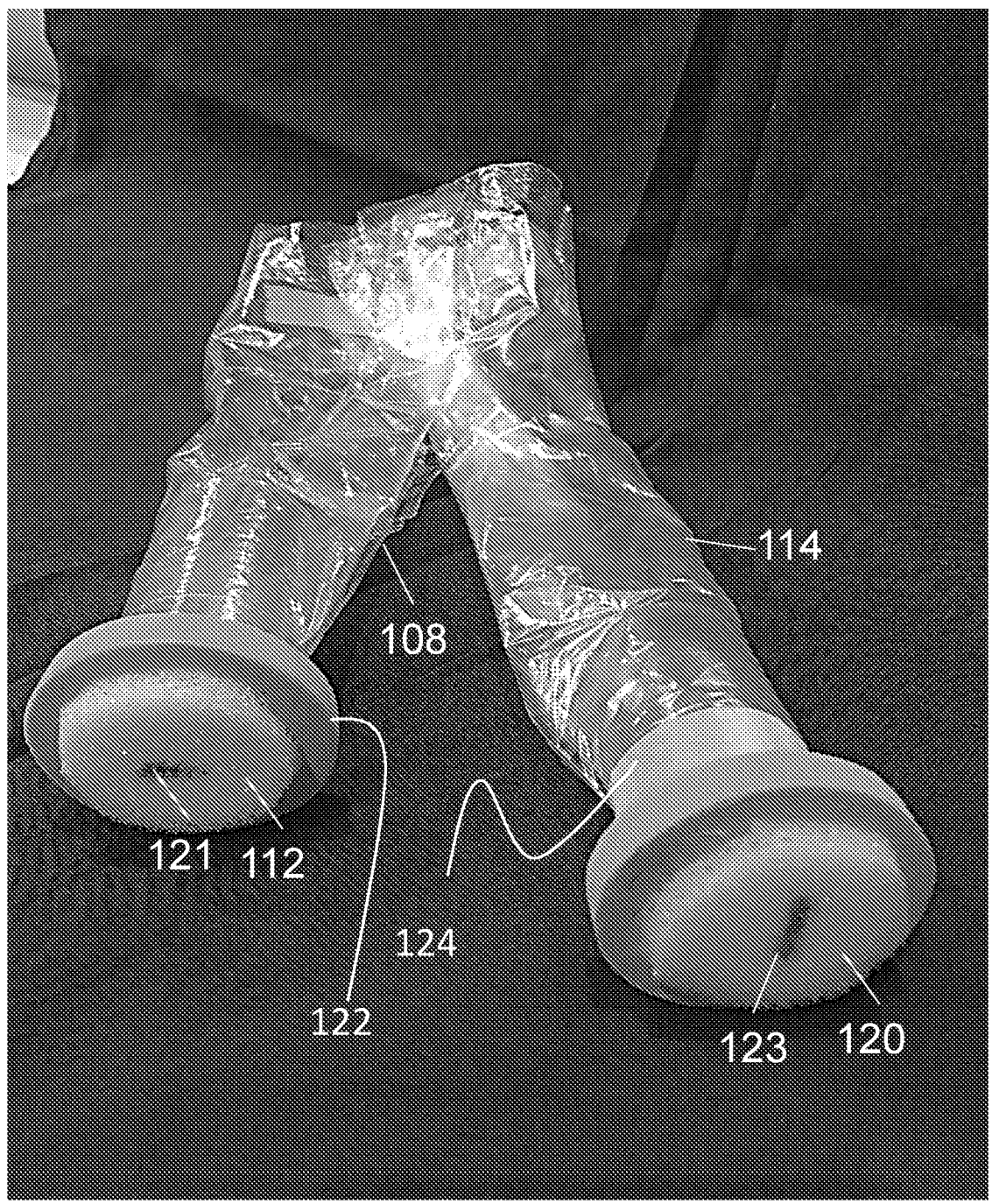
FIG. 4 is a perspective view of the two flexible sleeves, each having a seal member retained therein.

As shown FIG. 4, the flexible sleeves 108, 114 are provided as separate parts and fitted respectively to rigid portions 122, 124, to which there are affixed respective sealing members 112, 120. Proximal to the seal portion 102, the flexible sleeves 108, 114 are each attached to the instrument port 106. The flexible sleeves and the instrument port in this example are attached in a manner such that an air-tight surround is provided for a passage toward the orifice of the patient.

As an alternative to the embodiment of FIG. 4, the two separate sleeves 108, 114 may be provided as parts of a single component. For instance, the two flexible sleeves 108, 114 may be sleeve portions bifurcated from a single part adapted to connect to the instrument port 106. This embodiment can be expanded to include three or more sleeve portions which extend from a single connector part, in a construction akin to a manifold. As will be described in relation to a further embodiment, where the seal portion 102 does not include an instrument port, the sleeve(s) 108, 114 can attach directly to the seal portion 102, or the perimeter 104 of the seal portion 102.

The surgical instrument 111, 118 may be any instrument used for surgical procedures. Therefore, the sealing arrangement 112 and the flexible sleeve 108 are adapted to accept entry of a scope, such as an endoscope, which may be relevant in surgical or clinical examination or procedures. The flexible sleeve 108 further needs to be adapted to accommodate movement and manoeuvring of the surgical tool therein.

In the depicted embodiments, the seal portion 102 are provided as a mask adapted to be fitted over the nose and mouth of the patient. The seal portion 102, or at least the part of the seal portion 102 which is adapted to come into contact with the patient, particularly pressure sensitive areas of the patient, is preferably made from a material that is designed to be comfortable for the patient to wear, such as a silicon material. However, the seal portion 102 is not restricted to being a mask, and may be provided in any other form as long as it is adapted to be fitted over an orifice of a patient.

A perimeter portion 104 of the seal portion or mask 102 is adapted to be sealed onto the patient's face. This may be done by suction. For instance, the perimeter portion 104 comprises gel pads to facilitate the sealing onto the patient's face. In use, the patient's skin may additionally be moisturised prior to the sealing portion 102 being fitted, to strengthen the sealing properties. Alternatively, or simultaneously, the perimeter portion 104 may be sealed onto the patient by any or a combination of the following means: negative pressure, static force, the use of an adhesive material, or a gel. The perimeter portion 104 may further be adapted to be sealed onto the patient's face in a manner such that facial pressure is reduced. The protective device 100 are optionally equipped with straps for wrapping around the patient's head and holding the seal portion 102 into place to cover the patient's orifices.

Figure 2:
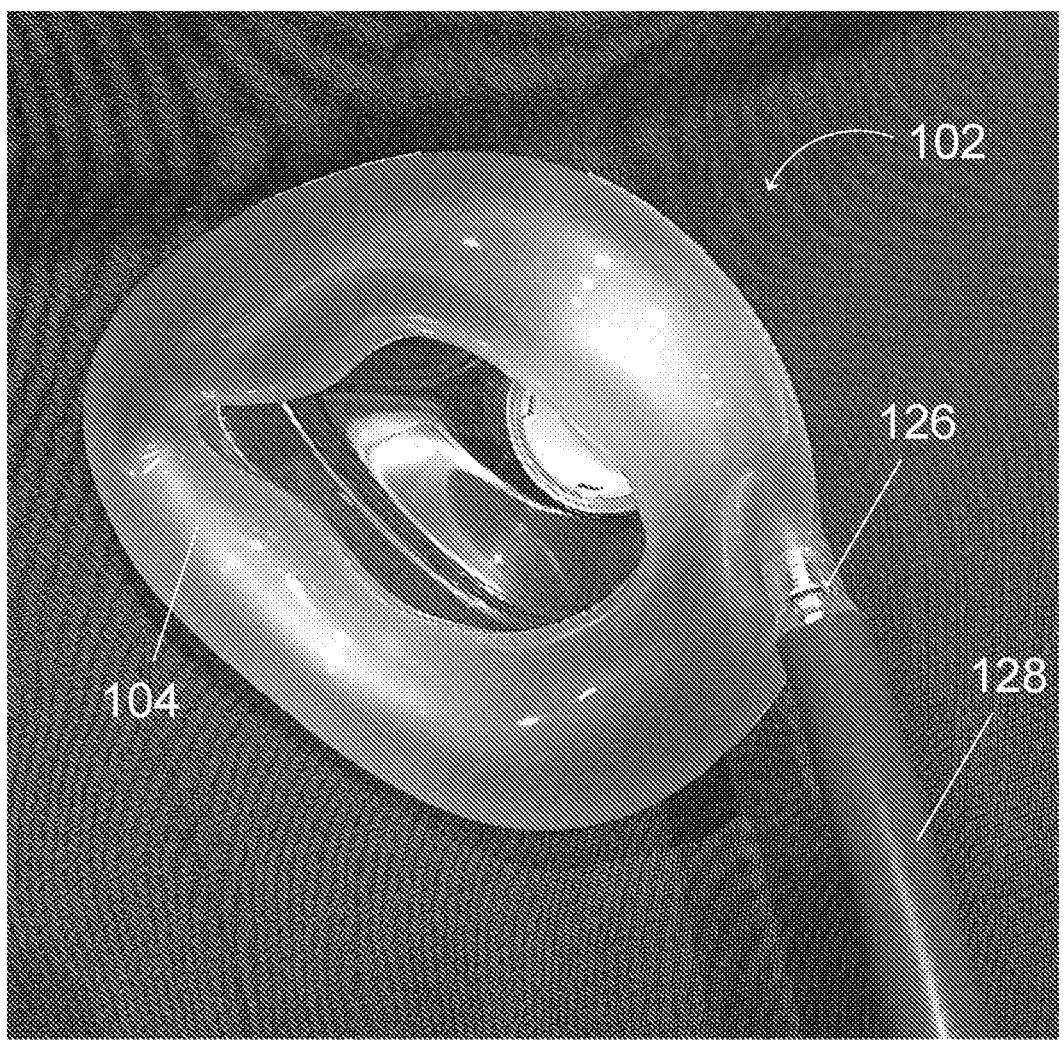
FIG. 2 is a bottom perspective view of a seal portion having a spout, of the protective device shown FIG. 1, with a tube fitted to the spout.
Figure 3:
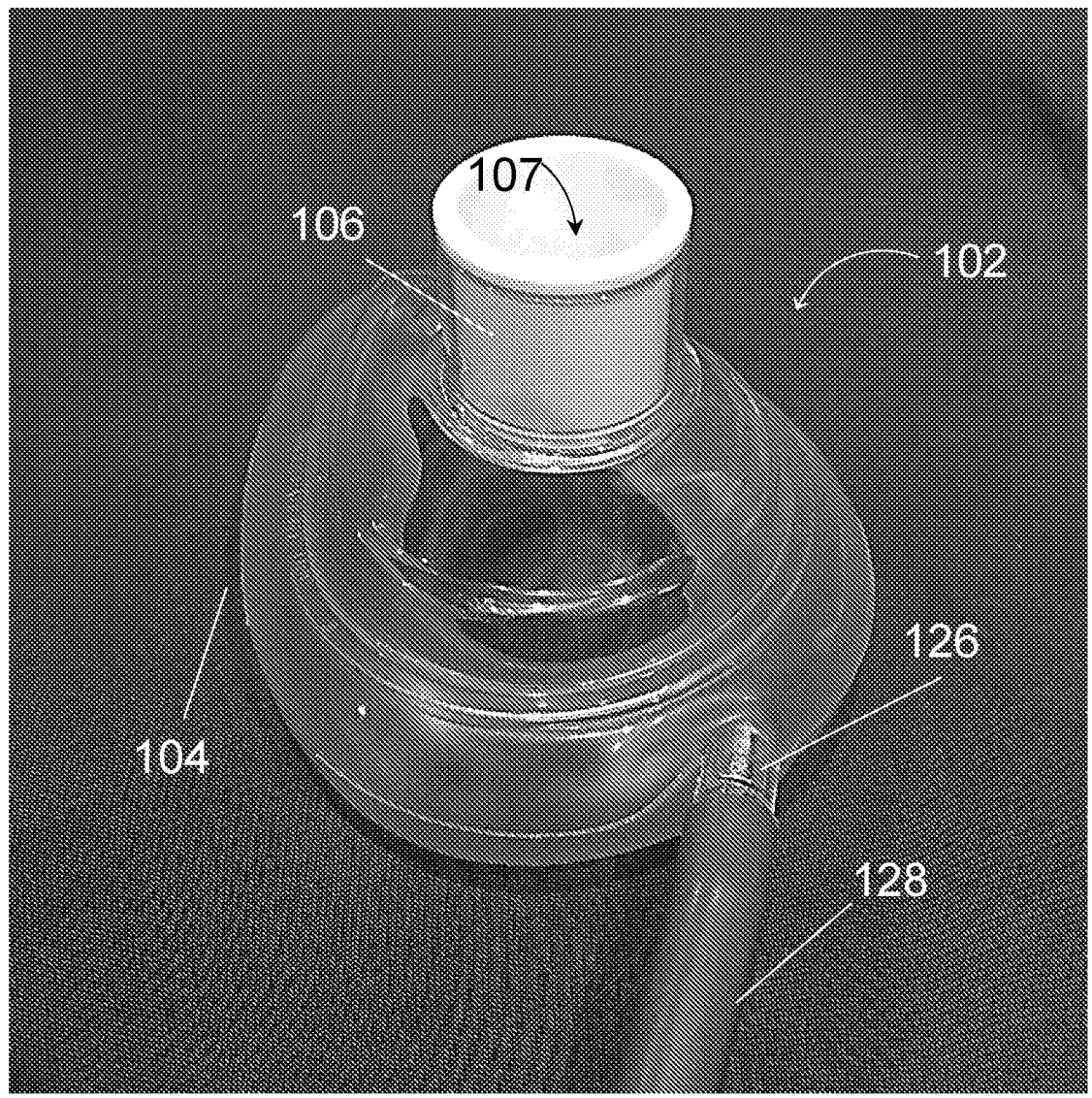
FIG. 3 is a top perspective view of the seal portion and an instrument port of the protective device shown in FIG. 1.
Figure 5:
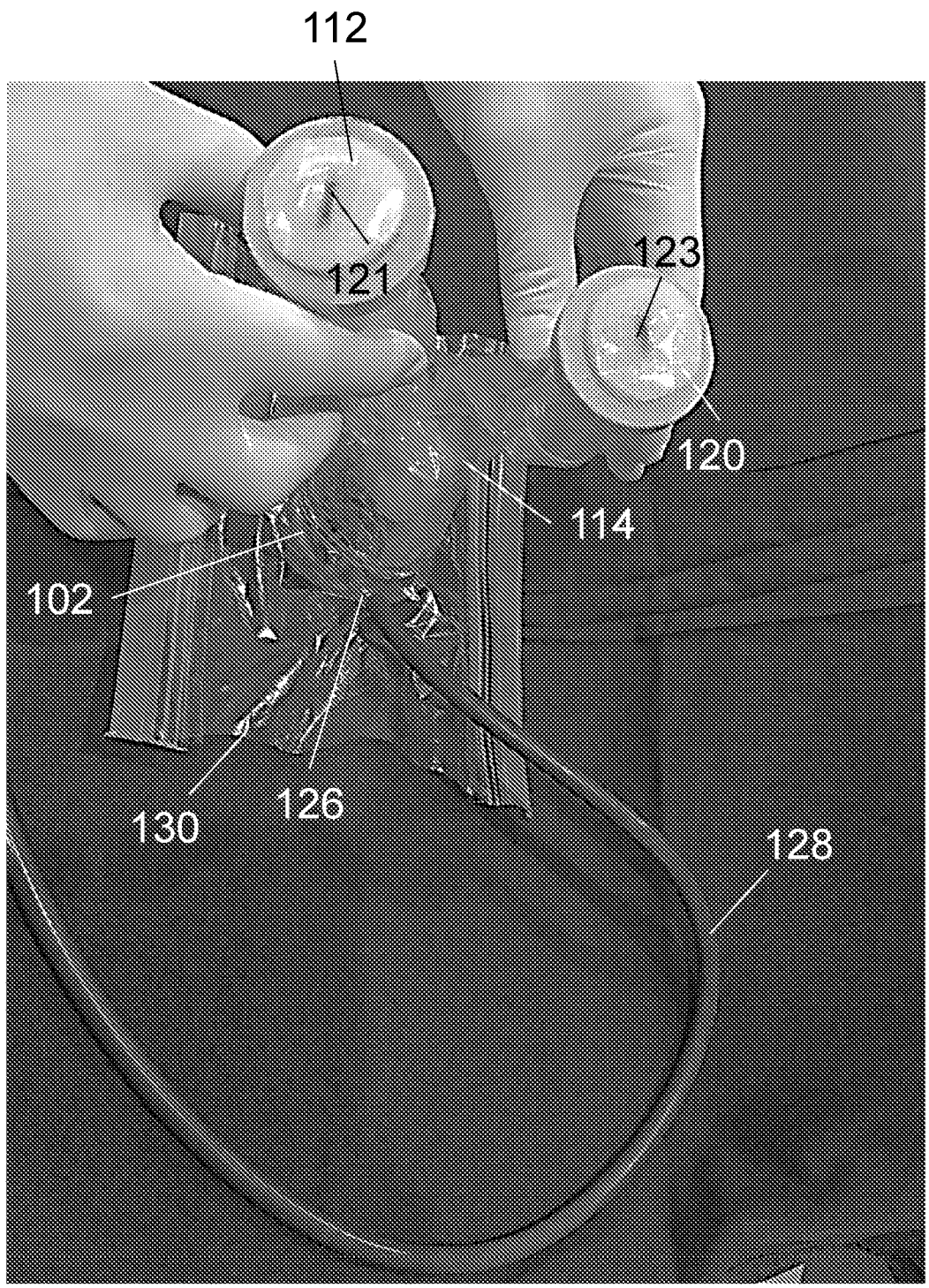
FIG. 5 is a perspective view of the flexible sleeves shown in FIG. 4, fitted onto the seal portion shown in FIG. 3.

As shown in FIGS. 2, 3, and 5, the seal portion 102 comprises an aperture or vent to delivery or conforms to an underlying oxygen delivery system and/or suction within a spout or nozzle 126. The spout or nozzle 126 can be adapted to connect with or accept there-through a tube for delivery of an anaesthetic to the patient, or it can be adapted for connection with or to allow passage there-through a suction tube 128 to remove air or particles from inside the seal portion 102 via negative pressure, or both. In some embodiments, two or more spouts or nozzles 126 may be provided, to simultaneously accommodate a suction tube and another tube for air or gas inflow.

It will be appreciated that the number of instrument ports 106 provided in the protective device 100 can be varied, as long as at least one instrument port 106 is provided. Each instrument port 106 may be attached or connected to a respective sleeve 108. Alternatively, the seal portion 102 may comprise more than one instrument port 106, and two or more of the instrument ports may be attached to one flexible sleeve which provides an air-tight surround for a passage toward said orifice. The sleeve 108 would thus need to be dimensioned according to accommodate the instrument ports 106 and the surgical tools 111 to be accepted by the instrument ports 106. Further alternatively, as shown in FIGS. 1 and 5, multiple flexible sleeves 108 may extend from a single instrument port 106. Embodiments may have combinations of one or more of the aforementioned arrangements to suit particular applications. For example, an embodiment with multiple instrument ports may have one instrument port which extends into a corresponding flexible sleeve, and two instrument ports in respective of which one flexible sleeve is provided to fit over or connect to both instrument ports. Another example may include at least one instrument port which each has a respective flexible sleeve, and another instrument port which connect to two flexible sleeves.

The flexible sleeve 108 (or 114) is preferably elongate in shape. Elongated flexible sleeves facilitate mobility for the healthcare professional, such as a surgeon, during a surgery procedure or clinical examination, while minimising the risk of the seal portion 102 such as a mask moving and possibly being dislodged during the procedure, which is not desired. The sleeve 108 (114) is made from a flexible material which is preferably see through, and more preferably transparent. It may be a deformable material, such as a polymeric material or a latex material. The flexible material may also be elastic and comprise an elastomeric material.

Different sealing arrangements 112 for sealing the distal opening of the flexible sleeves 108, 114 may be used in different embodiments. For example, in some embodiments, the sealing arrangement includes a sealing member 112 (120) made from a deformable material, through which a surgical instrument or scope can be inserted. The sealing member 112 may be a membrane, or a polymeric or elastomeric member which is puncturable by pushing the surgical instrument or scope there-through. It may comprise a weakened area through which a surgical instrument or scope could be pushed through, or multiple weakened areas if a single sleeve is provided for multiple surgical tools. The sealing member 112, 120 can each optionally comprise an aperture or a dimple which is shaped to facilitate guidance of the instrument to pass through the sealing member 112, 120 and into the passage in the respective flexible sleeve 108, 114, towards the instrument port 106 and the orifice of the patient. Embodiments which allow the access of multiple surgical tools through the same sealing member may therefore have multiple dimples or guiding apertures. The aperture or dimple may lead into a through opening that will be pushed open by the insertion of the instrument or surgical tool.

In FIGS. 1 to 5, the sealing members 112, 120 each comprise a foam material having a respective aperture 121, 123 (best seen in FIG. 4) provided therein, with a shaped opening to facilitate insertion of the surgical instrument 111, 118.

In some embodiments, the protective device 100 is constructed in one piece. The seal portion 102, the one or more instrument port 106, one or more flexible sleeves 108, 114 and respective sealing members 112, 120 may be moulded as a single part of the protective device 100. That is, the protective device 100 may be of an integral or unitary construction.

Alternatively, the protective device 100 is constructed by assembly of two or more parts. For example, the instrument port 106 may be co-moulded with one or more flexible sleeve 108, 114 as a single part, and the instrument port 106 is itself adapted to be coupled to the seal portion 102. The instrument port 106 and the seal portion 102 may be permanently attached via mechanisms such as fusing, bonding, via chemical or heat, or via adhesive. They may instead be detachably assembled. For instance they can respectively be provided with cooperating male and female connecting portions. The connecting portions may be adapted to be removably coupled together by screw threads, or via an interlocking arrangement. Other examples may include attachment by a friction fit between the components, or via a fastener, or via an intermediate coupler to which both components engage.

Similarly, the sealing member 112, 120 and the respective flexible sleeve 108, 114 can be moulded as a single piece. However, in alternative embodiments, the sealing member 112 (120) is a separate component to the sleeve 108 (114). For example, the sealing member 112, 120 may be directly fused, glued, or bonded onto the respective flexible sleeve 108, 114. It may be a deformable or compressible member that can be compressed to fit within the opening in the sleeve, and then allowed to expand to a larger size to thereby be retained by the wall of the sleeve. Alternatively, the sealing member 112, 120 may be fitted to an insert which is then attached to the sleeve 108, 114 in a manner such that a seal is provided between the insert and the flexible sleeve 108. For example, the flexible sleeve 108, 114 may comprise a deformable portion that can be made to stretch over the insert and retain it by friction. Or, the sealing member 112, 120 may include a deformable flange adapted to be stretched over a rim at the free end of the sleeve 108 to create a tight and secure fit.

The connection between the flexible sleeve(s) 108 and the instrument port 106 is achievable by different structural configurations. For example, he flexible sleeve 108 may be of an integral or unitary construction with the instrument port 106. Where the flexible sleeve 108 is separate from the instrument port 106, it may be fused, bonded, or otherwise attached to the instrument port 106, or vice versa. It may be dimensioned to fit over the instrument port 106 and be secured thereto by a clamp or fastener (or vice versa). The sleeve 108 and the instrument port 106 may be coupled together, e.g., as cooperating male and female connectors, or both engage with an intermediate coupler.

Likewise, in embodiments where the instrument port 126 is assembled onto the seal portion 102 rather than being integral or unitary with the seal portion 102, the instrument port 106 and the seal portion 102 may engage or connect to each other in different manners. Examples include permanent connection achieved by means such as by fusing, bonding, adhesive. Alternative examples also include detachable connections, such as interlocking engagements, engagement by friction or external fasteners.

Figure 7:
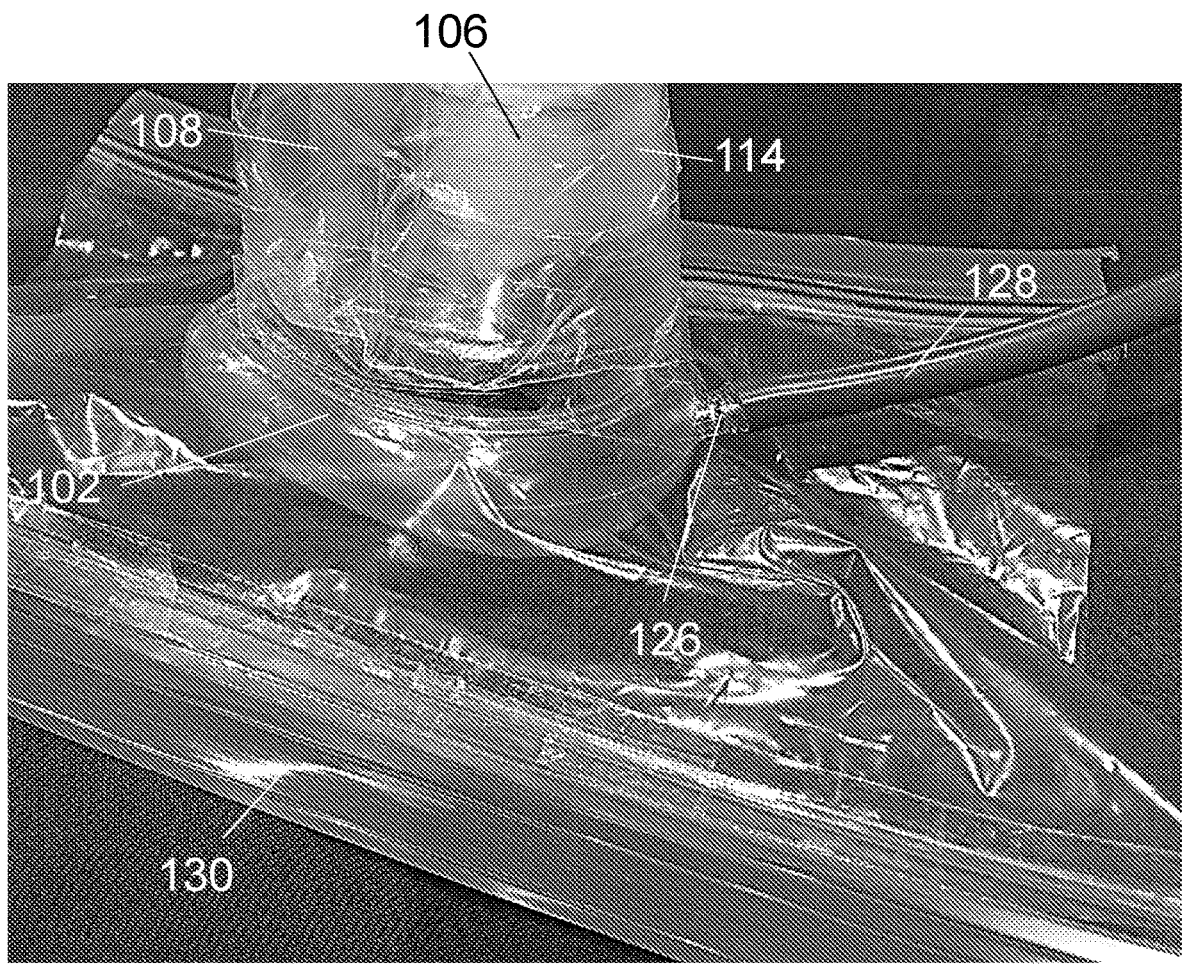
FIG. 7 is a partial perspective view of a protective device provided in accordance with another embodiment of the invention, depicting the seal portion, and a sleeve which fits over the seal portion.

FIG. 7 depicts an alternative embodiment. The protective device 100 shown in FIG. 7 is similar to that shown in FIG. 1. It includes the seal portion 102 comprising the instrument port 106. The instrument port 106 can be seen through the material of the flexible sleeves 108, 114 that are attached to the instrument port 106. The seal portion 102 comprises the spout or nozzle 126, which is adapted for connection with a suction device 128 to remove air or particles from inside the seal portion 102. This embodiment differs in that it includes a skirt 130 which is attachable to the patient's skin, in the area which surrounds the seal portion 102. The utility of the skirt 130 will be discussed further below in relation to FIG. 9 and FIG. 10.

Figure 8:
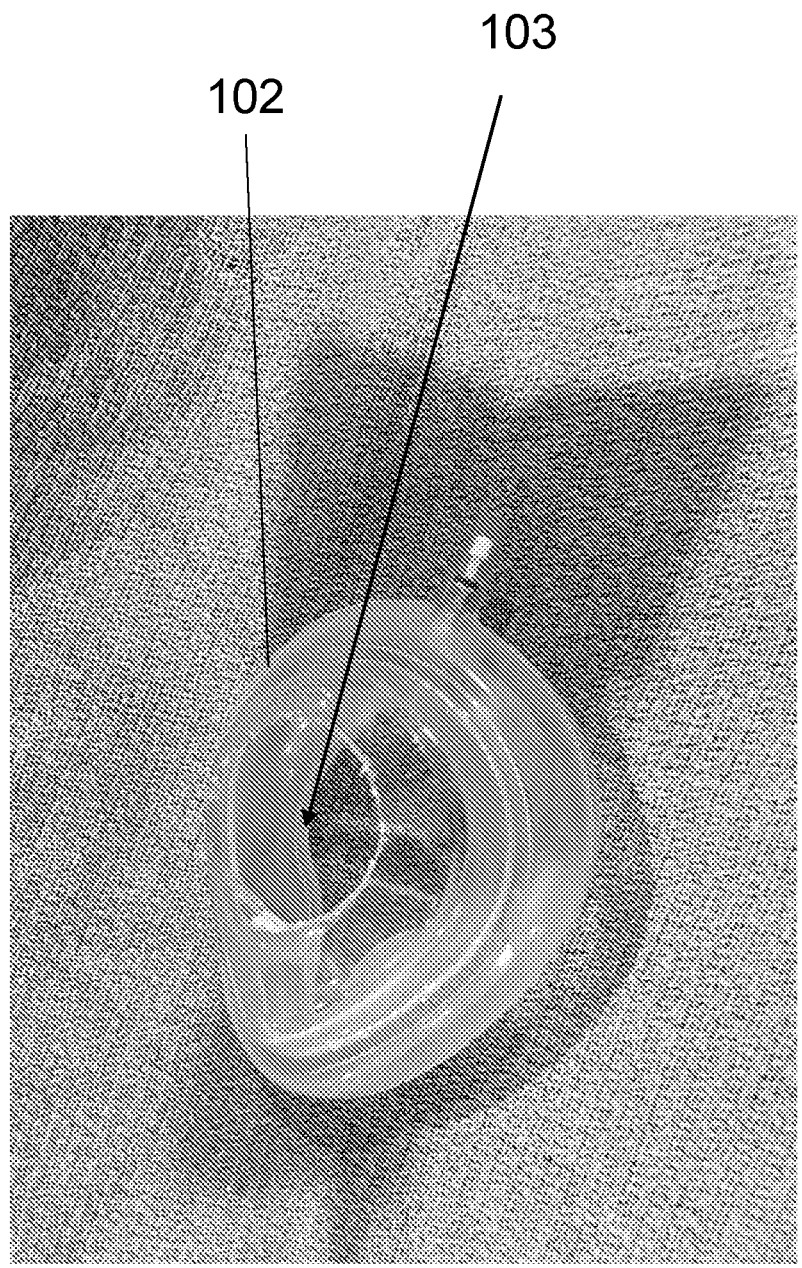
FIG. 8 is a perspective view of an alternative seal portion which does not have an instrument port.

FIG. 8 depicts a seal portion 102 in a further alternative embodiment. As shown, the seal portion 102 does not include an instrument port. Instead, the seal portion 102 includes an opening 103 which is positioned to be located over the patient's orifice in use. The sleeve(s) will be attached to the seal portion 102 adjacent this opening 103, or elsewhere on the protective device 100 to encompass this opening 103, so that the passage(s) defined by the sleeve(s) will enable access to the orifice via the opening 103, to enable manipulation of the surgical tools within the opening 103 and the patient's orifice, while substantially preventing or minimising the leakage of aerosolised particles from the orifice outside of the space enclosed by the seal portion 102 and the sleeve(s). This embodiment will have application where multiple tools need to be inserted into the patient's orifice at the same time, and ease of movement and manoeuvring of the tools is required for the performance of the procedure. Distal instrument port(s), or other sealing components permitting access into the sleeves, may be attached at the free ends of the sleeve 108,114 to enable entry of the instruments.

It is envisaged that further embodiments may combine both of the alternatives aforementioned with respect of FIG. 7 and FIG. 8. For instance, the embodiment shown in FIG. 9 and FIG. 10 combine both alternatives.

Figure 9:
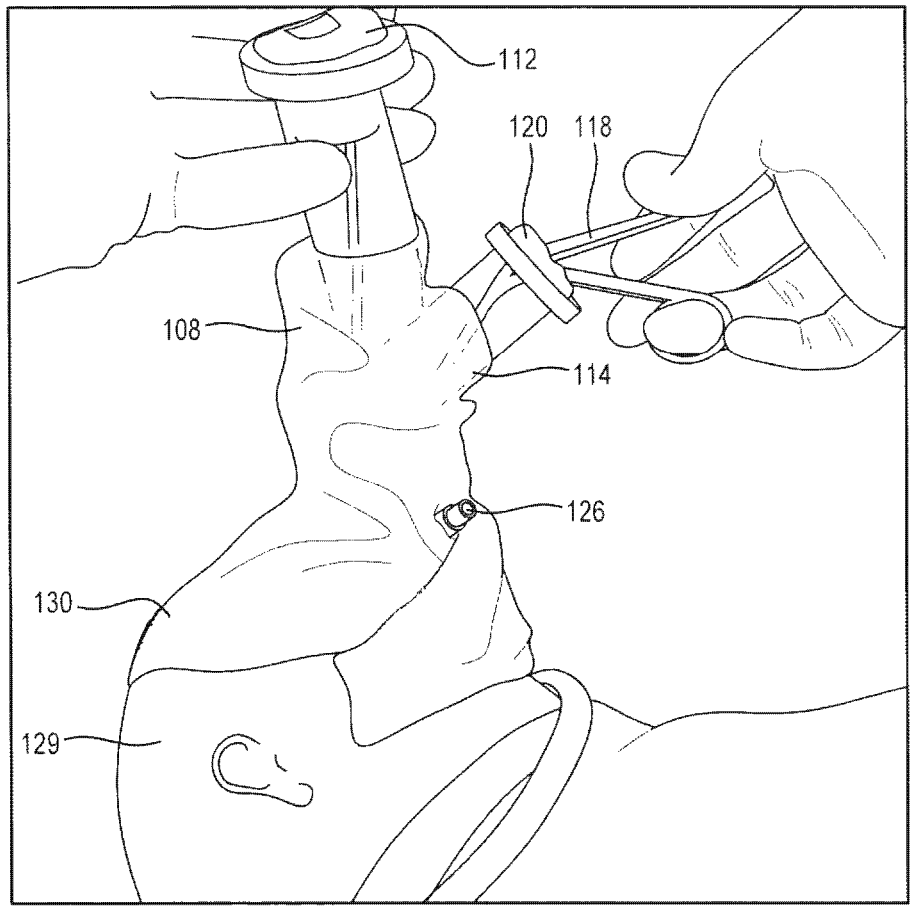
FIG. 9 is a perspective view the protective device shown in FIG. 7, fitted over a dummy.
Figure 10:
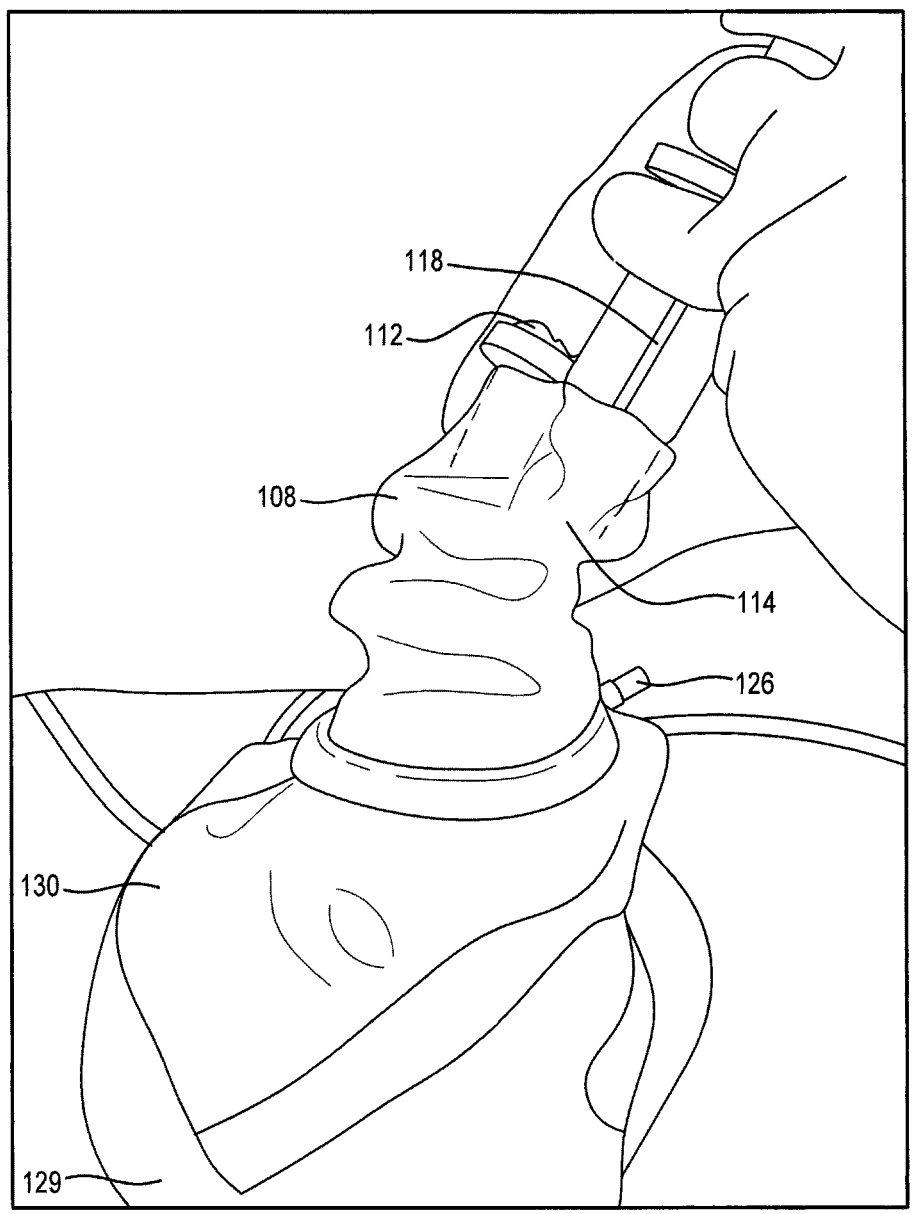
FIG. 10 is another perspective view of the protective device shown in FIG. 9, showing the sleeve covering the seal portion and further partially wrapping the forehead of the dummy.

FIG. 9 and FIG. 10 illustrate the protective device 100 provided in accordance with embodiments of the present disclosure wherein the protective device 100 is positioned on a patient's face (a dummy 129 is represented in the FIGS.) for use during surgical or clinical procedures. In some surgical applications, for example ENT surgical procedures, the patient would typically be anaesthetised and intubated with a breathing tube.

In use, during such surgical procedures, the protective device 100 is positioned onto the patient's face so that the seal portion 102 fits over the nose and mouth of the patient. The perimeter portion 104 is substantially sealed onto the patient's face. The seal portion 102 will typically fit over the breathing tube (not shown) where the breathing tube enters the mouth of the patient. To minimise leakage between the seal portion 102 and the breathing tube, additional sealing material may be provided to prevent or minimise leakage of aerosolised particles from the space enclosed by the protective device 100. Preferably, the seal conforms to the underlying intubation or other oxygen delivery tube, or nasal prongs, or evacuation device(s). This allows oxygen to be delivered by endotracheal intubation or nasal prongs, while the seal portion 102 is applied over the top of these devices.

In the example shown in FIG. 7, the protective device 100 further includes a skirt 130, which is adapted to be attached to the seal portion 102 and also the patient's skin in the area which surrounds the seal portion 102. The skirt 130 may be attached to the part of the seal portion 102 which covers over the patient's orifice, or a perimeter of the seal portion 102.

The skirt 130 may be sized such that it can further fit over an area larger than that defined by the perimeter of the seal portion 102. The skirt 130 can be provided at least partially over the seal portion 102 and further wrapped at least partially around the patient's face. The skirt 130 may be a waterproof adhesive film material, such as an OpSite® film, which will be adhered to the protective device 100 and also the patient's skin. It will also be tightly fitted over and thus adhered to any intubation tube over which the protective device 100 is positioned, facilitating a seal of the seal portion 100 over the intubation tube, and onto the patient's skin. Negative pressure may also be applied to the inside of the seal portion 102 to further improve the seal and location of the protective device 100 onto the patient.

In another embodiment, the skirt 130 is still of a flexible material which enables it to be fitted tightly over the intubation tube but does not have the adhesive layer. It may be held in place by, e.g., a medical gel substance, a negative pressure applied to the space enclosed by the seal portion, or both.

In other embodiments, the skirt 130 extends into the flexible sleeves 108, 114, the skirt 130 and sleeve(s) 108, 114 being a one-piece component. The sleeve(s) 108, 114 in these embodiments will therefore not engage or couple with the instrument port.

The protective device 100 shown in FIG. 7 is suited for applications in dentistry wherein the mouth of a patient is examined very closely. Other applications may include anaesthetics, gastroenterology, aesthetics and maxillofacial.

Remote and robotic operating applications are also envisaged such as in space wherein remote-control procedures by a technician/surgeon can be facilitated, but other staff located nearby will have minimal exposure to any leakage of particles, aerosolised particles, or droplets, from the patient.

The protective device 100 in accordance with embodiments of the present disclosure may also be used by a general practitioner when looking in the throat of a patient (e.g. when they use a tongue depressor) to see throat, tonsils, etc. The protective device 100 could also be adapted for robotic oral and oropharyngeal surgery, or in-room examinations, e.g. in ENT applications such as nasoendoscopy, wherein nasogastric scopes may be used. The protective device 100 could also be used for reducing blood splatter or fluid splatter during surgical procedures or clinical procedures.

The protective device 100, combining respective seals onto the patient (particularly embodiments which cover patient's face) and around surgical instruments or scope used during surgical or clinical procedures, is adapted to prevent leakage of aerosolized discharges from the patient's orifice outside of a space enclosed by the protective device 100, to reduce the situations in which wherein healthcare professionals need to wear extensive PPE. The protective device 100 in accordance with embodiments of the present disclosure is particularly advantageous in surgical or clinical applications, such as ENT surgery, as it provides a substantially safe, sealed, and re-sealable access for a "window" (simply viewing/looking in the nose and mouth) to visually inspect the patient. It also provides access of instruments required during surgical or clinical procedures, including scope equipped with a CCD camera or a fibre optic camera on a flexible tube, for the examination and undertaking of healthcare activities, especially wherein a patient's nose and/or mouth need to be accessed.

In the above, the protective device 100 can be wholly or partially provided as a single use device which is to be discarded after use. Alternatively, the protective device 100 may be in whole or in part be multi-use devices which can be sterilised and re-used.

Modifications and variations as would be apparent to a skilled addressee are determined to be within the scope of the present invention.

It is also to be understood that, if any prior art publication is referred to herein, such reference does not constitute an admission that the publication forms a part of the common general knowledge in the art, in Australia or any other country.

In the claims which follow and in the preceding description, except where the context requires otherwise due to express language or necessary implication, the word "comprise" or variations such as "comprises" or "comprising" is used in an inclusive sense, i.e., to specify the presence of the stated features but not to preclude the presence or addition of further features in various embodiments of the disclosure.

The invention claimed is:

1. A protective device for minimizing leakage of aerosols or aerosolized particles from an orifice of a patient, the orifice being either one or both of the patient's nose and mouth, the device comprising:
   a seal portion adapted to be fitted over the orifice of the patient, the seal portion including a cover, the cover being adapted to define a space over the patient's orifice, the seal portion having a perimeter portion adapted to be sealed around the orifice;
   one or more flexible sleeves each providing an air-tight surround defining a passage adapted to communicate with said orifice;
   each of the one or more flexible sleeves having an opening at an end thereof which is distal from the cover of said seal portion, the opening adapted to receive a sealing member;
   wherein the sealing member is adapted to receive therethrough a surgical instrument or scope, the sealing member being configured to prevent leakage from the passage,
   wherein the seal portion comprises or is connected to two or more instrument ports,
   and
   wherein at least one of the one or more flexible sleeves is provided over at least two of the two or more instrument ports.

2. The protective device of claim 1, wherein at least one of the one or more flexible sleeves is provided over a single one of the two or more instrument ports.

3. The protective device of claim 1, wherein two or more flexible sleeves are provided over one of the two or more instrument ports.

4. The protective device of claim 1, wherein each of the one or more flexible sleeves is elongated.

5. The protective device of claim 1, wherein the perimeter portion of the seal portion is sealed around the orifice by way of any one or more of the following: suction, negative pressure, an adhesive material, a static material, a polymeric material, moisture, a gel.

6. The protective device of claim 1, wherein the seal portion includes an aperture adapted for allowing air inflow or delivery of air into the seal portion from an air delivery device.

7. The protective device of claim 6, wherein said aperture is provided by a spout or a nozzle.

8. The protective device of claim 1, wherein the seal portion includes an aperture or vent adapted for insertion of, or connection with, a suction device to remove air or particles from inside the seal portion.

9. The protective device of claim 1, wherein the seal portion, the two or more instrument ports, and the one or more flexible sleeves are of an integral or unitary construction.

10. The protective device of claim 1, wherein the seal portion is made of a transparent material.

11. The protective device of claim 1, further comprising a skirt attached to the seal portion and adapted to be attached to the patient.

* * * * *